United States Patent [19]

Elbein

[11] Patent Number: 6,090,605
[45] Date of Patent: Jul. 18, 2000

[54] PURIFIED PORCINE KIDNEY L-FUCOSE KINASE

[75] Inventor: Alan D. Elbein, Little Rock, Ark.

[73] Assignee: The Board of Trustees of the University of Arkansas, Little Rock, Ark.

[21] Appl. No.: 09/149,303

[22] Filed: May 8, 1998

Related U.S. Application Data

[63] Continuation-in-part of application No. 08/596,907, Mar. 11, 1996, abandoned.
[51] Int. Cl.[7] ....................................................... C12N 9/12
[52] U.S. Cl. ..................... 435/194; 424/94.61; 424/94.5; 530/415; 530/416
[58] Field of Search .......................... 435/194; 424/94.61, 424/94.5; 530/415, 416

[56] References Cited

PUBLICATIONS

Park et al. "Purification to Apparent Homogeneity and Properties of Pig Kidney L–Fucose Kinase," J. Biol. Chem. (Mar. 6, 1998) 273(10):5685–5691.

*Primary Examiner*—Francisco Prats
*Attorney, Agent, or Firm*—Benjamin Aaron Adler

[57] ABSTRACT

The present invention provides an enzyme L-fucokinase isolated from porcine kidney and in homogeneously purified form. The enzyme has a native molecular weight of 440 kDa based on gel filtration, a subunit molecular weight of about 110 kDa based on SDS PAGE, an optimal pH of about 8.0, and wherein said enzyme catalyzes the phosphorylation of L-fucose and does not phosphorylate D-glucose, D-galactose and D-mannose.

8 Claims, 10 Drawing Sheets

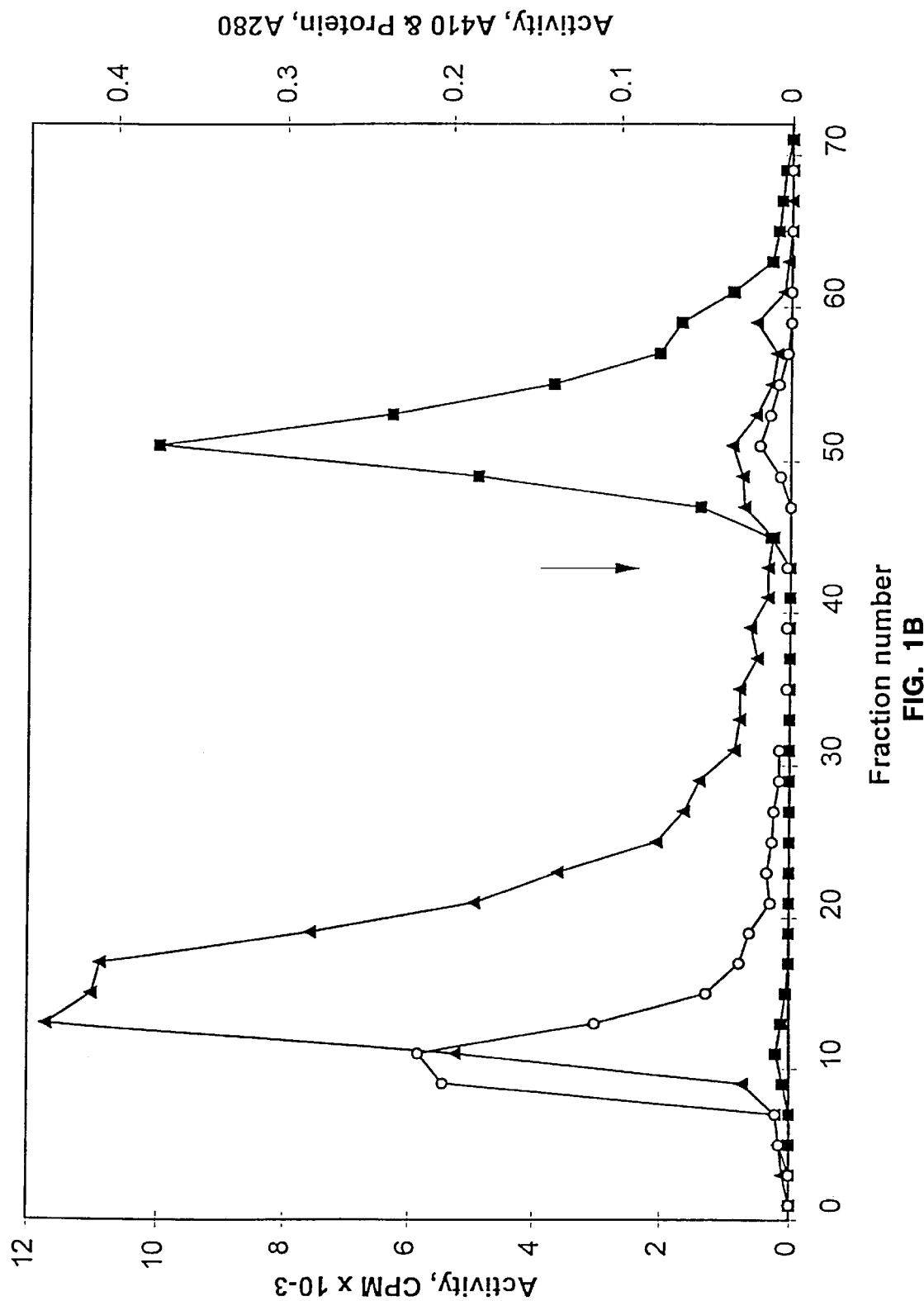

SEQUENCE LISTING

```
<160> NUMBER OF SEQ ID NOS: 3

<210> SEQ ID NO 1
<211> LENGTH: 16
<212> TYPE: PRT
<213> ORGANISM: Sus scrofa
<220> FEATURE:
<223> OTHER INFORMATION: Peptide from Endo Lys C digestion of 110 kDa
      subunit of porcine kidney L-fucose kinase

<400> SEQUENCE: 1
```

-continued

```
Val Asp Phe Ser Gly Gly Trp Ser Asp Thr Pro Pro Leu Ala Tyr
                5                   10                  15
Glu

<210> SEQ ID NO 2
<211> LENGTH: 18
<212> TYPE: PRT
<213> ORGANISM: Sus scrofa
<220> FEATURE:
<223> OTHER INFORMATION: Peptide from Endo Lys C digestion of 110 kDa
      subunit of porcine kidney L-fucose kinase

<400> SEQUENCE: 2

Thr Gly Ile Arg Asp Trp Asp Leu Trp Asp Pro Asp Thr Pro Pro
                5                   10                  15
Thr Glu Arg

<210> SEQ ID NO 3
<211> LENGTH: 12
<212> TYPE: PRT
<213> ORGANISM: Sus scrofa
<220> FEATURE:
<223> OTHER INFORMATION: Peptide from Endo Lys C digestion of 110 kDa
      subunit of porcine kidney L-fucose kinase

<400> SEQUENCE: 3

Leu Ser Trp Glu Gln Leu Gln Pro Cys Leu Asp Arg
                5                   10
```

PURIFIED PORCINE KIDNEY L-FUCOSE KINASE

CROSS REFERENCE TO RELATED APPLICATION

This application is a continuation in part of U.S. Ser. No. 08/596,907, filed Mar. 11, 1996, now abandoned.

FEDERAL FUNDING NOTICE

The present invention was created in part using funds from a grant from the National Institutes of Health (HL-17783). Consequently, the United States government has certain rights in this invention.

BACKGROUND OF THE INVENTION

1. Field of the Invention

The present invention relates generally to the fields of enzymology and carbohydrate chemistry. More specifically, the present invention relates to purified, homogeneous porcine kidney L-fucokinase and uses thereof.

2. Description of the Related Art

L-Fucose (6-deoxy-L-galactose) is an important sugar in animal cells since it is involved in various recognition reactions of glycoproteins and glycolipids (1). Thus, oligosaccharides that have α1,2-linked L-fucose are precursors for blood group A and B antigens (2). In the Lewis blood group antigens, Galβ1,3 (Fucα1,4) GlcNAc-R and Fucα1, 2Galβ1,3(Fucα1,4)GlcNAc-R are determinants for Lewis[a] and Lewis[b] blood group antigens. In addition, fucosylated and sialylated oligosaccharides have been found to be the recognition molecules for the E- and P-selectins, two members of the selectin family of cell adhesion molecules (3). These selectins and their fucosylated- (and sialylated) ligands are important in inflammation and in the recognition of leukocytes for endothelial cells (4).

The primary pathway for the formation of L-fucose in procaryotic and eucaryotic cells is from D-mannose via an internal oxidation-reduction of GDP-D-mannose and this product is epimerized to produce GDP-L-fucose (5–8). However, studies in rats showed that radiolabeled L-fucose could be incorporated into glycoproteins (9,10), suggesting an alternate route for activation of L-fucose. An L-fucokinase that synthesizes β-L-fucose-1-phosphate (11), and a GDP-L-fucose pyrophosphorylase (12) were partially purified from pig liver. However, the fucokinase preparation had rather broad substrate specificity with regard to sugar and nucleoside triphosphate, probably because of contaminating enzymes, such as hexokinase in the partially purified fraction.

The prior art is deficient in the lack of purified pig kidney fucokinase. The present invention fulfills this longstanding need and desire in the art.

SUMMARY OF THE INVENTION

The present invention describes the purification to near homogeneity of the pig kidney fucokinase. This enzyme preparation was very specific for L-fucose and the only other sugar that could be phosphorylated, at about 10% of the rate with L-fucose, was D-arabinose. This fucokinase is also quite specific for ATP as the phosphate donor. This enzyme should be valuable for the synthesis of large amounts of L-fucose-1-P, as well as for the formation of radiolabeled fucose-1-P.

L-Fucokinase was purified to apparent homogeneity from the cytosolic fraction of pig kidney. The purified enzyme had a molecular weight of about 440 kDa on a column of Sephacryl S-300, and gave a single protein band of 110 kDa on SDS gels. The 110 kDa band became labeled in a concentration dependent manner by azido-ATP[$^{32}$P]. The enzyme had a pH optimum of about 8.0 and required a metal ion for activity. $Mg^{++}$ was the best divalent cation with optimum activity occurring at a concentration of about 3 mM. The enzyme was quite specific for L-fucose as the sugar substrate and ATP as the phosphate donor. The only other sugar that was phosphorylated at about 10% the rate of L-fucose was D-arabinose. The $K_m$ for L-fucose was determined to be 27 μM and that for ATP was estimated to be 600 μM. The kinase activity was inhibited in a dose-dependent manner by GDP-L-fucose with a $K_i$ of about 10 μM. This inhibition was quite specific for this nucleotide and may have physiological significance. The product of the reaction of [$^3$H]L-fucose and ATP was isolated by ion-exchange chromatography and paper chromatography. The radioactive fucose product fucose-1-P was characterized by its susceptibility to mild acid hydrolysis and by proton NMR. Thus in 0.05 N HCl at 100° C., the product completely lost its charge in less than 3 minutes. The charge was also removed by treatment with alkaline phosphatase. Proton NMR also demonstrated that the product was L-fucose-1-P, and that the phosphate is attached in a β-configuration.

In one embodiment of the present invention, there is provided an enzyme L-fucokinase in an isolated and homogeneously purified form.

In another embodiment of the present invention, there is provided an enzyme L-fucokinase in its native state having a molecular weight of 440 kilodaltons based on gel filtration, an optimal pH of about 8.0, and having the activity to catalyze the phosphorylation of L-fucose but does not phosphorylate D-glucose, D-galactose and D-mannose.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the steps in the purification of fucokinase. In FIG. 1B, the concentrated enzyme from the Sephacryl S-300 was applied to a 1.5×10 cm column of aminohexyl agarose. The column was washed with 300 mM NaCl in Buffer C, and was eluted with a gradient of 300 to 700 mM NaCl in Buffer C (arrows indicate the start of the gradient). Fractions were assayed for fucokinase (filled squares), α-mannosidase (filled triangles), and protein (o-----o).

DETAILED DESCRIPTION OF THE INVENTION

Figure 1A:
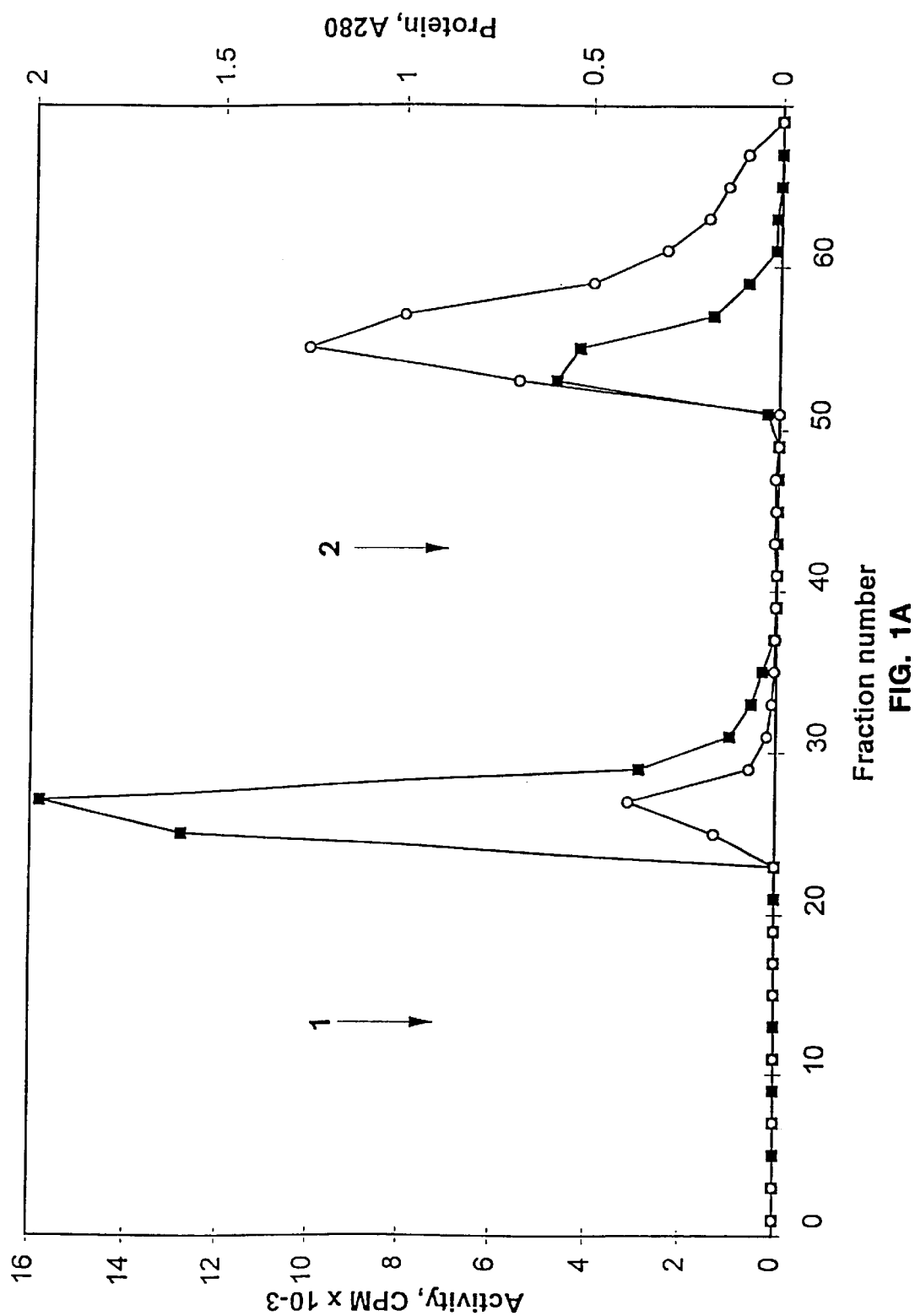
In FIG. 1A, the enzyme fraction from Macro-Prep Methyl HIC was applied to a 2.5×10 cm of column of hydroxylapatite that had been equilibrated with Buffer B. The column was eluted with a 0 to 50 mM gradient of $KH_2PO_4$ in Buffer B (arrow 1) and then with a 0 to 150 mM linear gradient of $K_2HPO_4$ in Buffer B (arrow 2).

The present invention is directed to the enzyme L-fucokinase in an isolated and homogeneously purified form. Preferably, the enzyme L-fucokinase is isolated and purified to homogeneity from pig kidney. Even more preferably, the enzyme L-fucokinase in its native state has a molecular weight of 440 kilodaltons based on gel filtration, has an optimal pH of about pH 8.0, and wherein said enzyme has the activity to catalyze the phosphorylation of L-fucose and does not phosphorylate D-glucose, D-galactose and D-mannose.

As shown by the present invention, enzyme L-fucokinase has a greater activity in the presence of a divalent cation selected from the group consisting of magnesium and iron than the activity it has when not in the presence of magnesium or iron. Furthermore, the enzyme L-fucokinase has a decreased activity in the presence of a divalent cation selected from the group consisting of copper, zinc and mercury than the activity it has when in the presence of magnesium or iron. More specifically, the L-fucokinase enzyme requires magnesium for optimal activity.

As shown by the present invention, the L-fucokinase enzyme activity is highest with ATP as a nucleoside phosphate donor and wherein said enzyme activity in the presence of a non-ATP nucleoside triphosphate is about 2% of the activity of the enzyme with ATP. Further, the enzyme is a homotetrameric protein with catalytic subunits each having a molecular weight of about 110 kDa. Generally, the L-fucokinase enzyme is specific for sugars having an L-galactose configuration at carbons 2, 3 and 4.

The following examples are given for the purpose of illustrating various embodiments of the invention and are not meant to limit the present invention in any fashion.

EXAMPLE 1
Materials

[$^3$H]L-Fucose (52 Ci/mmol) and other radioactive sugars were purchased from American Radiolabeled Chemicals, Inc., or New England Nuclear Co. L-fucose-1-P, non-radioactive sugars, and nucleoside diphosphate sugars were obtained from Sigma Chemical Co. Various adsorbents were obtained from the following sources: DE-52 from Whatman Chemical Ltd., hydroxylapatite from Biorad, omega-aminohexyL-Agarose and Sephacryl S-300-HR from Sigma Chemical Co. The following materials were obtained from Biorad: Sodium dodecylsulfate (SDS), Acrylamide, Bisacrylamide, Comassie blue, Protein assay reagent. All other chemicals were from reliable chemical sources, and were of the best grade available.

EXAMPLE 2
Assay of Fucokinase Activity

Fucokinase activity was assayed by measuring the production of L-fucose-1-P from [$^3$H]L-fucose and ATP. The incubation mixtures contained the following components (final concentrations) in a total volume of 150 μl: L-fucose, 0.1 mM; ATP, 5 mM; $MgSO_4$, 5 mM; Tris-HCl buffer, pH 8.0, 65 mM; and various amounts of enzyme at the different stages of purification. Incubations were at 37° C. for 10 minutes, and reactions were terminated by heating the reaction mixtures in a boiling water bath for 1 minute. The incubation mixtures were then applied to a column of DE-52 contained in a Pasteur pipette, and the column was washed with at least 5 column volumes of 10 mM $(NH_4)HCO_3$ to remove the unbound material. The [$^3$H]fucose-1-P was then eluted with 500 mM $(NH_4)HCO_3$. Aliquots of the eluates were assayed for their radioactive content by subjecting a portion to scintillation counting.

EXAMPLE 3
Purification of the Fucokinase

For the preparation of the cytosolic fraction, pig kidneys were obtained from a local slaughterhouse and were transported to the laboratory on ice. The fresh kidneys were defatted and cut into pieces which were washed with cold distilled water. Each kidney piece was homogenized in a Waring blender in 2 volumes of Buffer A (30 mM Tris-HCl, pH 7.8, containing 10% glycerol, 1 mM EDTA, 1 mM PMSF and 1 mM P-mercaptoethanol). The homogenates were centrifuged at 12,000×g for 30 minutes in a Beckman J-21 centrifuge. The supernatant liquid was removed and filtered through 6 layers of cheesecloth. The filtered supernatant liquid was then further centrifuged at 100,000×g for 45 minutes. The clarified supernatant liquid was then used as the starting crude extract. All operations in the purification were done at 0 to 4° C., unless otherwise specified. In all cases, fresh kidneys were used as the starting material for purification since the fucokinase activity was much lower after freezing the tissue.

EXAMPLE 4
DE-52 Column Chromatography

A 5×16 cm column of DE-52 was prepared and the column was equilibrated with Buffer A. The supernatant liquid from the ultracentrifugation of 400 g of kidney (i.e., about 500 ml of supernatant liquid) was applied to the column, and the column was washed well with Buffer A and then with 800 ml of 0.1 M KCl. The fucokinase was eluted with 1000 ml of a 0.1 to 0.5 M gradient of KCl. Nine ml fractions were collected and every other fraction was assayed for activity and for protein. Active fractions were pooled and brought to 60% saturation by the addition of solid ammonium sulfate. After standing on ice for 15 minutes, the precipitate was isolated by centrifugation and dissolved in Buffer A, containing 1 M ammonium sulfate.

EXAMPLE 5
Hydrophobic Chromatography on Macro-Prep Methyl HIC Support

The dissolved ammonium sulfate fraction was applied to a 2.5×20 cm column of Macro-Prep Methyl HIC Support that had been equilibrated with Buffer A, containing ammonium sulfate. The column was then washed with the equilibration buffer. The kinase was eluted from the column with a linear gradient of 1 to 0 M ammonium sulfate in Buffer A. Active fractions were pooled and concentrated to about 30 ml on an Amicon filtration apparatus using a PM 30 membrane. The concentrated enzyme was then dialyzed against Buffer B (30 mM HEPES buffer, pH 7.6, containing 1 mM β-mercaptoethanol and 10% glycerol).

EXAMPLE 6
Chromatography on Hydroxylapatite

The dialyzed enzyme was loaded onto a 2.5×10 cm column of hydroxylapatite that had been equilibrated with Buffer B. The column was washed with the same buffer and then eluted with a 0 to 50 mM linear gradient of $KH_2PO_4$ in Buffer B. Under these conditions, the kinase bound to the column but not as tightly as other proteins in the preparation. Thus, about 60 to 70% of the enzyme emerged from the column at 15 to 25 mM $KH_2PO_4$. Some of the enzyme did remain on the column and could be eluted with the bulk of the protein at about 50 mM $K_2HPO_4$, in Buffer B.

EXAMPLE 7
Gel Filtration Chromatography

Active fractions, eluted from the hydroxylapatite column, were pooled and concentrated to about 2 ml on the Amicon apparatus. The concentrated enzyme preparation was applied to a 1.5×95 cm column of Sephacryl S-300 that had been equilibrated with Buffer C (25 mM HEPES buffer, pH 7.1, containing 1 mM β-mercaptoethanol and 10% glycerol). Four ml fractions were collected and assayed for fucokinase activity. Active fractions were pooled and concentrated to a small volume.

EXAMPLE 8
Chromatography on Aminohexyl Agarose

The concentrated enzyme fraction from Sephacryl was applied to a 1.5×10 cm column of aminohexyl agarose, that had been equilibrated with Buffer C. The column was washed with 300 mM NaCl in Buffer C, and the kinase was eluted with 160 ml of a linear gradient of 300 to 700 mM NaCl in Buffer C. Fractions containing the active enzyme were pooled and the NaCl was remolded by filtration on an Amicon apparatus and stored at −80° until used for various experiments. The most purified enzyme preparation gave a single protein band of 110 kDa on SDS gels, but was found to still be contaminated with α-mannosidase activity (see below) which also had a molecular weight of 110 kDa on SDS PAGE. Thus, fractions from the aminohexyL-agarose column were assayed for fucokinase and α-mannosidase, and fractions containing fucokinase activity were incubated with the $N_3$-ATP[$^{32}$P] probe and examined by SDS-PAGE and autoradiography to identify the fucokinase.

EXAMPLE 9
Polyacrylamide (native) Gel Electrophoresis

Preparative polyacrylamide gel electrophoresis was done at 4° C. in tubes containing 7% acrylamide and 10% glycerol as described by Laemmli (15), and using Tris buffer. The pH of the stacking gel was 6.7 and that of the resolving gel was 8.9. The samples of fucokinase were made up to 10% with respect to sucrose and contained bromophenol blue. During electrophoresis, the current was maintained at 3 mA/gel, and the temperature was kept at 4° C. Two samples were run in parallel. One gel was stained with Coomassie blue to detect proteins, while the other gel was cut into 0.25 cm pieces and the enzyme was eluted by overnight diffusion at 4° C. into Buffer A. The various elutions were then assayed for enzymatic activity.

Figure 4A:
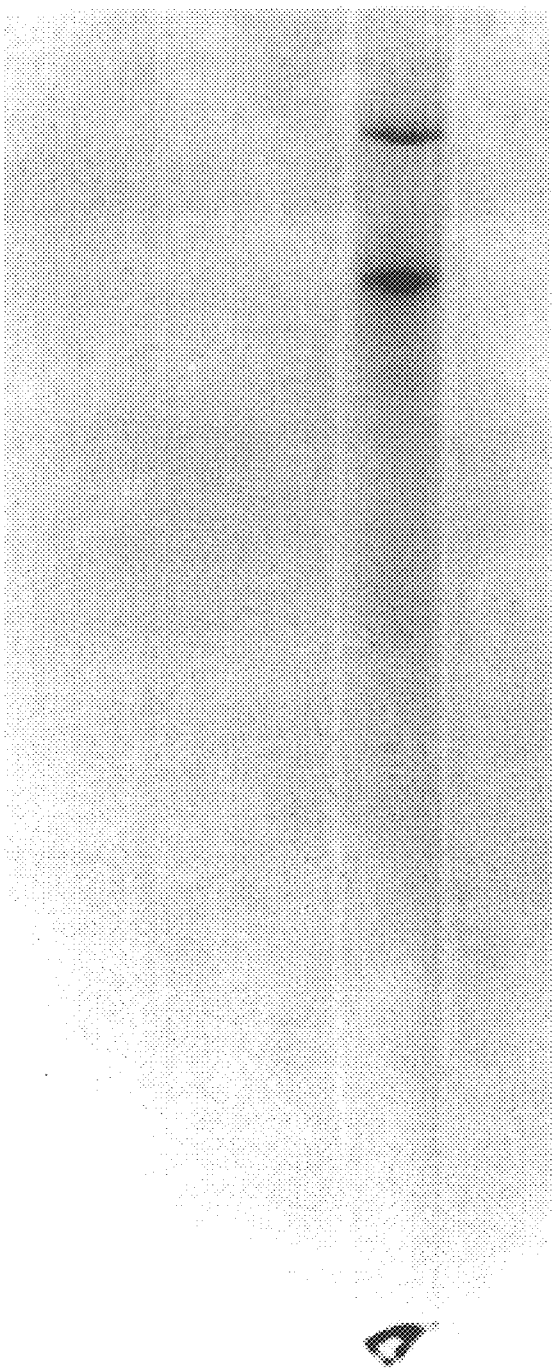
FIG. 4 shows native gel electroxphoresis of the purified fucokinase. Enzyme was purified as indicated in Table I and gave a single protein band of 110 kDa on SDS gels (FIG. 2, lane 7). This enzyme preparation was subjected to nondenaturing gel electrophoresis as indicated in the methods section and gave two protein bands (FIG. 4A). The proteins were visualized with Coomassie blue. The native gel removed from the tube and loaded on top of a slab gel and subjected to SDS-PAGE in the second dimension to determine the subunit composition of the two native protein bands. These proteins were also stained with Coomassie Blue (FIG. 4B).
Figure 4B:
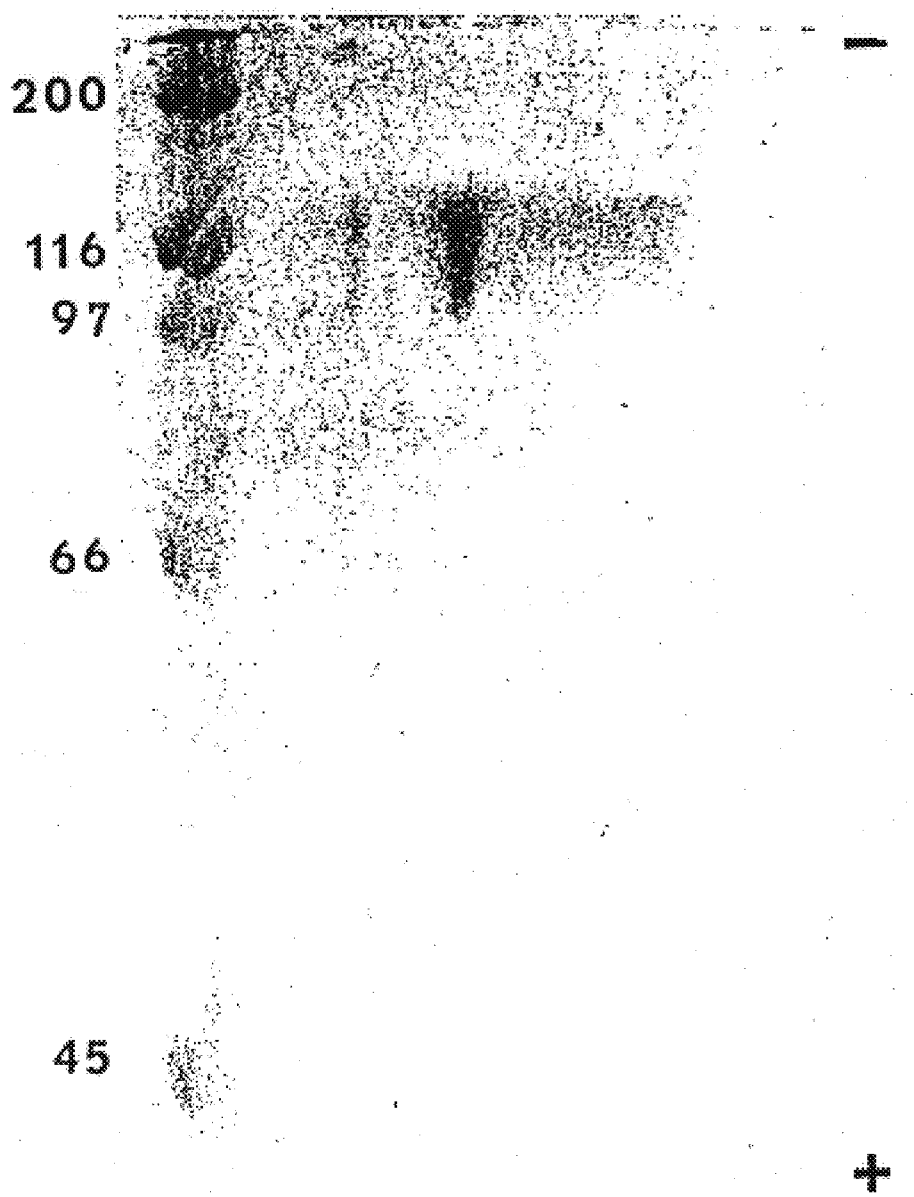

On native gels, the fucokinase (MW 440 kDa, lower band of FIG. 4A) was separated from the α-mannosidase (upper band of FIG. 4A). In order to show that both of these bands were composed of 110 kDa subunits, the native gel was removed from the tube and laid on its side on top of an SDS slab gel and polymerized to that gel. Standard proteins were also combined in a native gel and added to the top of the slab gel. The proteins in the native gels were then subjected to SDS-PAGE as seen in FIG. 4B.

EXAMPLE 10
Photoaffinity Labeling of the Fucokinase with 8-Azido-ATP [$^{32}$P]

Enzyme, at various stages of purity, was mixed with 8-azido-ATP[$^{32}$P] in buffer, and allowed to incubate for 20 sec. in an ice bath. 8-Azido-ATP[$^{32}$P] was prepared as previously described (16). After incubation, the reaction mixture was exposed to short wave UV light for about 90 sec. to activate the azido group, and the protein was subjected to SDS gel electrophoresis to separate the proteins. The gels were dried and exposed to film to locate the radioactive bands and were also stained with Coomassie blue to locate the various proteins. The specificity of the labeling was determined by examining the effect of various concentrations of unlabeled ATP or other nucleotides on the labeling of the protein by $N_3$-ATP[$^{32}$P]. Various controls were also run, such as one in which exposure to UV was omitted.

EXAMPLE 11
Characterization of the Product

The radioactive sugar phosphate produced in the reaction was isolated by ion exchange chromatography from large scale incubations of $^3$H-fucose and ATP with purified enzyme. The radiolabeled peak that eluted from DE-52 with a gradient of 0 to 250 mM (NH$_4$)HCO$_3$ was lyophilized several times to remove the bicarbonate, and was then subjected to hydrolysis in various concentrations of HCl to determine the location of the phosphate group. Sugar-1-phosphates are quite sensitive to mild acid hydrolysis (0.05 N), and the phosphate group is lost fairly rapidly, whereas phosphate residues on other hydroxyl groups are quite stable to these conditions. In addition, the product was analyzed by proton NMR to determine the location and anomeric configuration of the phosphate group. Three hundred mHz proton NMR and $^{31}$P-decoupled (GARP) NMR on the sample of L-fucose-1-P were performed on a Bruker ARX300 NMR. Data were acquired in D$_2$O at pH 6.0.

EXAMPLE 12
Other Methods

Protein was measured by the method of Bradford (17), using bovine serum albumin as the standard. The molecular weight of the native fucokinase was determined by gel filtration on Sephacryl S-300 and that of the subunit(s) by SDS gel electrophoresis. A number of molecular weight standards were run including: thyroglobulin (Mr 669,000), apoferritin (Mr 443,000), β-amylase (Mr 200,000), alcohol dehydrogenase (Mr 150,000), bovine serum albumin (Mr 66,000), and cytochrome C (Mr 12,000).

EXAMPLE 13
Purification of the Fucokinase

The pig kidney fucokinase was purified about 5000-fold with a recovery of activity of about 21% using the procedure described above. FIG. 1 shows two of the key steps in the purification procedure, i.e., chromatography on hydroxylapatite (FIG. 1A) and chromatography on an aminohexyl agarose column (FIG. 1B). The hydroxylapatite step gave about a 10 fold purification whereas chromatography on aminohexyL-agarose gave better than a 6-fold purification. TABLE I presents a summary of the purification procedure showing the changes in specific activity at each step, and the recovery of activity. Based on gel filtration the native enzyme emerged from the column in the same area as apoferritin and had an estimated molecular weight of about 440 kDa.

Figure 2:
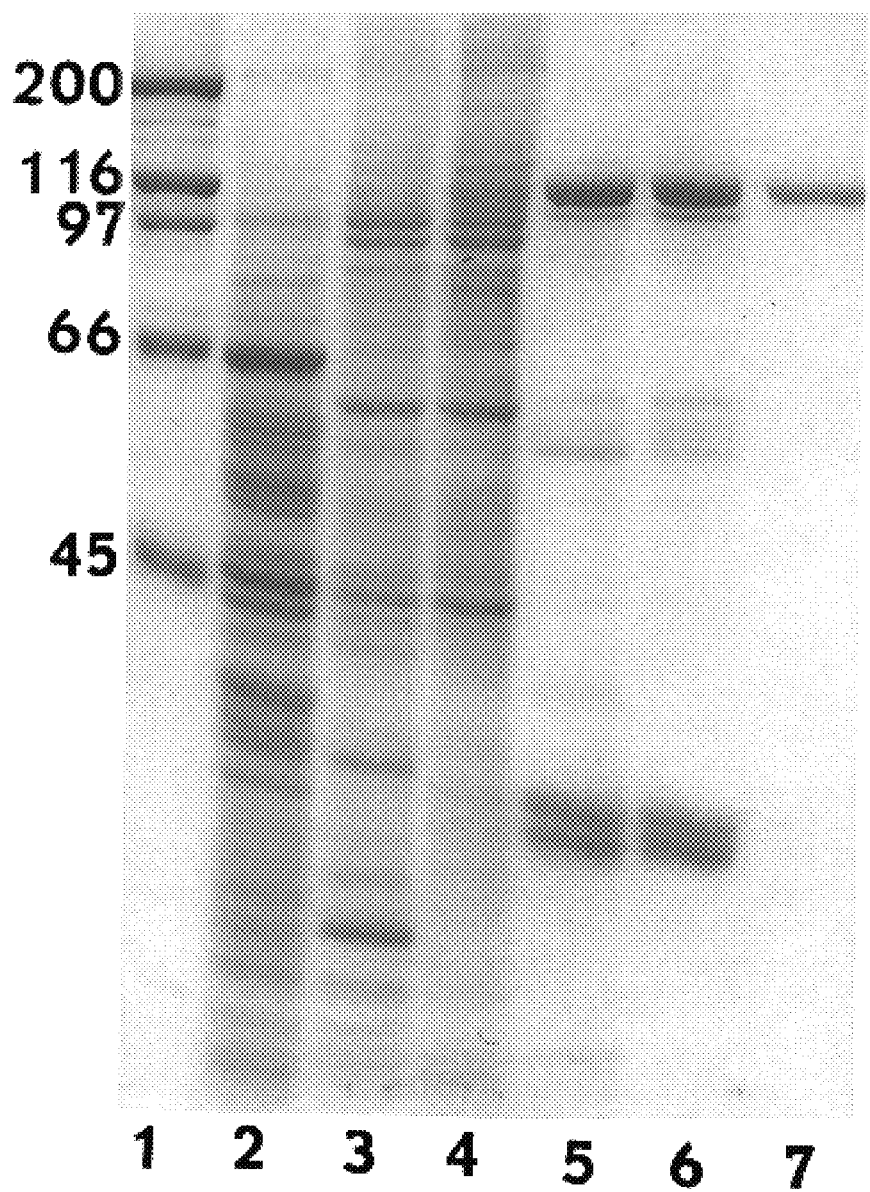
FIG. 2 shows the SDS-PAGE of the L-fucokinase at various stages of purification. The protein fraction (Lanes 2–6, about 30 μg protein; Lane 7 about 10 μg protein) at each step of purification was heated in 1% SDS, containing β-mercaptoethanol, and subjected to electrophoresis in 10% gels. The proteins were detected by staining with Coomassie blue. Lane 1 shows the protein standards; Lane 2, the crude cytosol; Lane 3, DEAE-cellulose; Lane 4, Marco prep methyl HIC; Lane 5, hydroxylapatite; Lane 6, Peak from Sephacryl S-300; Lane 7, purified enzyme from aminohexyl agarose.
Figure 3:
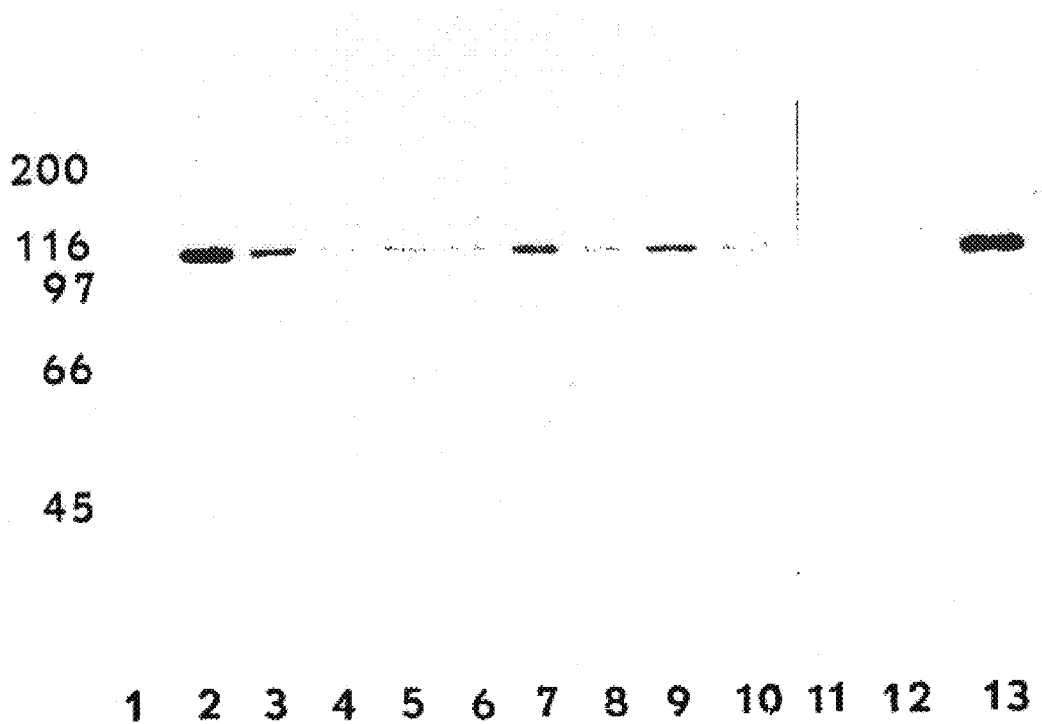
FIG. 3 shows photoaffinity labeling of the fucokinase with azido-ATP[$^{32}$P]. The purified enzyme was incubated for 20 seconds with azido-ATP[$^{32}$P], and the mixture was exposed to UV for 90 seconds. The reaction was stopped by adding loading buffer and the mixture subjected to SDS-PAGE. Radioactive bands were detected by exposure to film. Lanes are as follows: Lane 1, Probe+enzyme, but no UV; Lane 2, Probe+enzyme+UV; Lanes 3 through 6. Probe+enzyme+0.3, 0.6, 0.9, and 1.2 mM ATP+exposure to UV light; lanes 7 and 8, 0.6 and 1.2 mM GTP+probe+exposure to UV light: lanes 9 and 10, 0.6 and 1.2 mM ITP+probe+exposure to UV light. In lanes 11 and 12, the enzyme was incubated with $N_3$-GTP [$^{32}$P] and then exposed to UV light (lane 12) or not exposed to UV light (lane 11). Lane 13 is a control of enzyme+$N_3$-ATP[$^{32}$P]+exposure to UV light.

The purified enzyme was subjected to SDS gel electrophoresis as shown in FIG. 2. The initial crude extract showed a number of protein bands (lane 2), while the most purified preparation (lane 7) gave one major protein band with a molecular weight of about 110 kDa. That this band was indeed the L-fucokinase was demonstrated by the fact that it was specifically labeled by the photoprobe, azido-ATP[$^{32}$P]. Thus, as seen in FIG. 3, incubation of enzyme with $N_3$-ATP[$^{32}$P] gave a single labeled band at the 110 kDa region (Lane 2), but no labeled protein band was seen in the absence of exposure to UV light (Lane 1). The labeling was shown to be specific since it was inhibited in a dose-dependent manner by the addition of increasing amounts of unlabeled ATP (i.e., 0.3, 0.6, 0.9, 1.2 mM) to the incubation mixtures (Lanes 3–6). On the other hand, GTP at 0.6 and 1.2 mM (Lanes 7,8) or ITP, at 0.6 or 1.2 mM (Lanes 9,10) were considerably less effective in inhibiting the reaction. Lanes 11–13 of FIG. 3 show the results of another experiment designed to determine whether 8-$N_3$-GTP[$^{32}$P] could label the fucokinase. Lane 12 shows that incubation with this probe did not give rise to labeled protein, whereas incubation with $N_3$-ATP[$^{32}$P] did result in labeling of the 110 kDa protein (Lane 13). These experiments indicate that the fucokinase is quite specific for ATP.

In addition, when various fractions from the aminohexyl agarose column (FIG. 1B, fractions 48–56) were incubated with the $N_3$-ATP[$^{32}$P] probe, maximum labeling of the 110 kDa band was coincident with maximum fucokinase activity i.e., fractions 48, 50 and 52) (data not shown). These data provide convincing evidence that the 110 kDa band is the fucokinase.

The 110 kDa protein was cut from the gel and sent to Harvard Microsystems for amino acid sequencing. One peptide, obtained by Endo lys C digestion, was sequenced, and a BLAST search indicated significant homology to α-mannosidase. The purified enzyme preparation was found to have strong fucokinase activity, but also had readily detectable α-mannosidase activity. Although much of the α-mannosidase activity was removed on the aminohexyl agarose column, some activity still emerged with the fucokinase in fractions 46–56 (FIG. 1B). This enzyme preparation gave a single sharp band at 110 kDa on SDS gels as shown in FIG. 2, lane 7.

The fucokinase could be separated from the α-mannosidase by native gel electrophoresis. Thus as seen in FIG. 4A, gel electrophoresis of the enzyme preparation from the aminohexyL-agarose column on native gels gave 2 protein bands, one with an estimated molecular weight of 440 kDa, and a slower migrating band (FIG. 4A). The gel was sliced into 2.5 mm sections and the proteins were eluted into buffer and assayed for activity. The fucokinase activity was only associated with the lower band, while α-mannosidase was found in the upper, slower-moving band. When this native gel with the two bands was then subjected to SDS-PAGE in a second dimension (FIG. 4B), both the 440 kDa protein and the slower moving protein gave a single protein band of 110 kDa. These data indicate that both the fucokinase and the α-mannosidase are composed of 110 kDa subunits, but the native enzymes are quite different in size or charge.

The 110 kDa subunit isolated from the 440 kDa protein (FIG. 4B) was subjected to Endo lys C digestion, peptide isolation, and amino acid sequencing of several of the well-separated peptides. The amino acid sequences of three peptides were as follows:

PEPTIDE 1.

VDFSGGWSDTPPLAYE                (Seq. ID NO.:1)

PEPTIDE 2

(T)(G)IRDWDLWDPDTP(P)(T)ER      (Seq. ID NO.:2)

PEPTIDE 3

LSWEQLQPCLDR                    (Seq. ID N.:3)

These sequences do not show significant homology to any known sequences in the BLAST search.

TABLE I

Purification of Pig Kidney Fucokinase

| Purification Step | Protein (mg) | Total Activity (Units)* | Specific Activity (Units/mg Protein) | Fold | Yield (%) |
| --- | --- | --- | --- | --- | --- |
| 1. Crude Extract | 22000.0 | 5620 | 0.2555 | | 100 |
| 2. DE-cellulose | 1000.0 | 5560 | 5.56 | 21.89 | 8.9 |
| 3. Maco-Prep. Methyl. HIC | 232.5 | 4050 | 17.42 | 68.37 | 72.1 |
| 4. Hydroxylapatite | 13.2 | 2446 | 185.30 | 726.7 | 43.5 |
| 5. Sephracryl S-300 | 11.5 | 2497 | 221.96 | 870.4 | 44.4 |
| 6. Aminohexyl Agarose | 0.95 | 1210 | 1273.68 | 4994.8 | 21.5 |

*Units are nmole of fucose-1-P produced in 1 minutes.

EXAMPLE 14

Properties of the Fucokinase

The purified enzyme was studied to determine its substrate specificity, as well as various other properties of the enzymatic reaction. The enzyme showed a typical pH profile from 5.5 to 8.0 using MES and HEPES buffers, with a sharp pH optimum at about 8.0 in HEPES buffer. However, the pH curve on the alkaline side, between 8.0 and 9.0 in Tris buffer, did not show a sharp optimum. The activity in Tris buffer, pH 8.0, was about 80% of that in HEPES buffer, pH 8.0 (data not shown).

Figure 5:
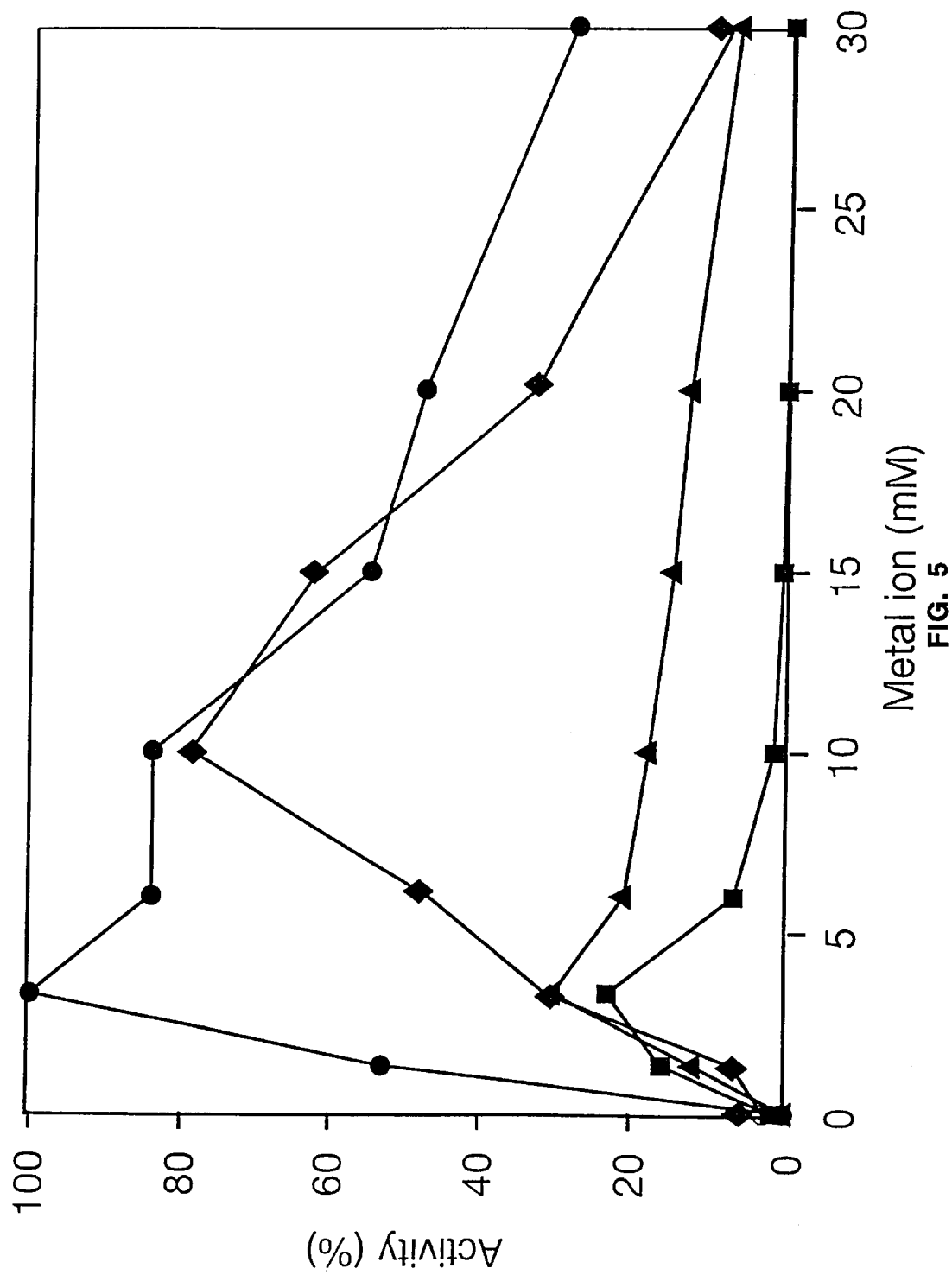
FIG. 5 shows the effect of metal ions on fucokinase activity. Increasing concentrations of the metal ions shown were added to incubations of the purified enzyme with $^3$H-fucose and ATP, and the formation of fucose-1-P was measured as described below. Metal ions tested were as follows: $Mg^{++}$, filled circles; $Fe^{++}$, filled diamonds; $Co^{++}$, filled triangles; $Mn^{++}$, filled squares.

The enzyme had an absolute requirement for a divalent cation for activity. As shown in FIG. 5, $Mg^{++}$ gave the best stimulation with optimum activity being seen at 3 mM concentration. $Fe^{++}$ also stimulated the enzyme to nearly the same degree as $Mg^{++}$, but in this case, optimum activity occurred at about 10 mM. $Co^{++}$ and $Mn^{++}$ were also stimulatory with maximum activity occurring at about 3 to 5 mM, but the maximum activity was only about 25% to 33% of that observed with $Mg^{++}$. A variety of other metal ions were tested and found to be inactive, including $Ca^{++}$, $Cu^{++}$, $Fe^{+++}$, $Hg^{++}$, $Mo^{++}$, $Ni^{++}$, and $Zn^{++}$. However, when $Cu^{++}$, $Zn^{++}$ and $Hg^{++}$ were added at 1 mM concentrations to incubations containing $Mg^{++}$, they completely inhibited activity.

EXAMPLE 15

Sugar Specificity of Purified Fucokinase

The specificity of the kinase for various sugar substrates was examined in two different ways. In the first set of experiments, various radiolabeled sugars were tested as phosphate acceptors for the purified enzyme using the ion-exchange chromatography method for assay of activity. TABLE II shows the results of this experiment. It can be seen that of all the sugars tested, L-fucose was by far the best substrate and was readily phosphorylated. D-Arabinose, which has the same configuration at carbons 1 through 4 as L-fucose, was also a reasonable substrate for phosphorylation, and was about 10% as effective as L-fucose. On the other hand, all of the other sugars were ineffective as phosphate acceptors.

TABLE II

Sugar Specificity of Purified Fucokinase

| Radiolabeled Sugar Added | *Specific Activity (nmole/mg protein) |
| --- | --- |
| L-fucose | 11.8 |
| D-arabinose | 1.1 |
| D-glucose | 0.3 |
| D-ribose | 0 |
| D-mannose | 0 |
| D-galactose | 0 |
| D-xylose | 0 |

The concentration of radiolabeled sugar was 100 μM.

EXAMPLE 16

Inhibition of Fucose Phosphorylation by Various Monosaccharides

Although it was possible to get a reasonable assessment of the sugar specificity of the kinase from the above experiment, it was not possible to test sugars such as D-fucose, since these sugars are not available in radioactive form. Thus, these unlabeled sugars were tested for their ability to inhibit the phosphorylation of [$^3$H]L-fucose. The rationale for this experiment is that a sugar that inhibits the phosphorylation of L-fucose would probably compete with L-fucose for the phosphorylation (i.e., active) site. TABLE III shows that as expected unlabeled L-fucose was a reasonable inhibitor of the activity and unlabeled D-arabinose also inhibited although considerably less so than the L-fucose. Interestingly enough, D-fucose and L-rhamnose were ineffective as inhibitors, as was 2-deoxyglucose, or other sugars. These data indicate that the configuration of the sugar at carbons 1 through 4 must be in the L-galactose configuration to be a substrate or inhibitor.

TABLE III

Inhibition of Fucose Phosphorylation by Various Monosaccharides

| Monosaccharides Added* | Relative Activity (%) |
| --- | --- |
| None | 100 |
| L-fucose | 23 |
| D-fucose | 102 |
| D-arabinose | 80 |
| D-mannose | 100 |
| D-glucose | 100 |
| D-galactose | 100 |
| D-rhamnose | 102 |
| D-xylose | 103 |
| D-ribose | 96 |
| 2-deoxy-D-glucose | 92 |

Unlabeled monosaccharides were added at 500 μM concentrations.
Radiolabeled L-fucose as the substrate was present at 100 μM.

EXAMPLE 17
Specificity of Fucokinase for Phosphorate Donor

The specificity of the nucleoside triphosphate was also examined by testing the ability of a variety of nucleotides to serve as phosphate donors in the phosphorylation of [$^3$H]L-fucose. TABLE IV demonstrates that the kinase is very specific for ATP as the phosphate donor and shows less than 2% activity with any other nucleoside triphosphate. In addition, no activity is observed with any nucleoside diphosphates or monophosphates.

TABLE IV

Specificity of Fucokinase for Phosphorate Donor

| Nucleotide Added* | Specific Activity (nmoles/mg protein/10 min) |
| --- | --- |
| ATP | 4.05 |
| ITP | 0.10 |
| UTP | 0.04 |
| CTP | 0.05 |
| GTP | 0.09 |

*Nucleotides were added at 1 mM concentration. Inactive nucleotides included: ADP, CDP, GDP, UDP, AMP, CMP, GMP, UMP.

EXAMPLE 18

The effect of concentration of the substrates, L-fucose and ATP, on the velocity of the reaction was determined. The $K_m$ for L-fucose was determined at saturating concentrations of the other substrates, i.e., 5 mM ATP and 5 mM $Mg^{++}$. The data was plotted by the method of Lineweaver and Burke, and the $K_m$ for L-fucose was determined to be 27 μM (data not shown). A similar experiment was performed with ATP. In this case, the reactions were done in the presence of 5 mM $Mg^{++}$ and 100 μM L-fucose. The $K_m$ for ATP was estimated to be 600 μM (data not shown).

Figure 6:
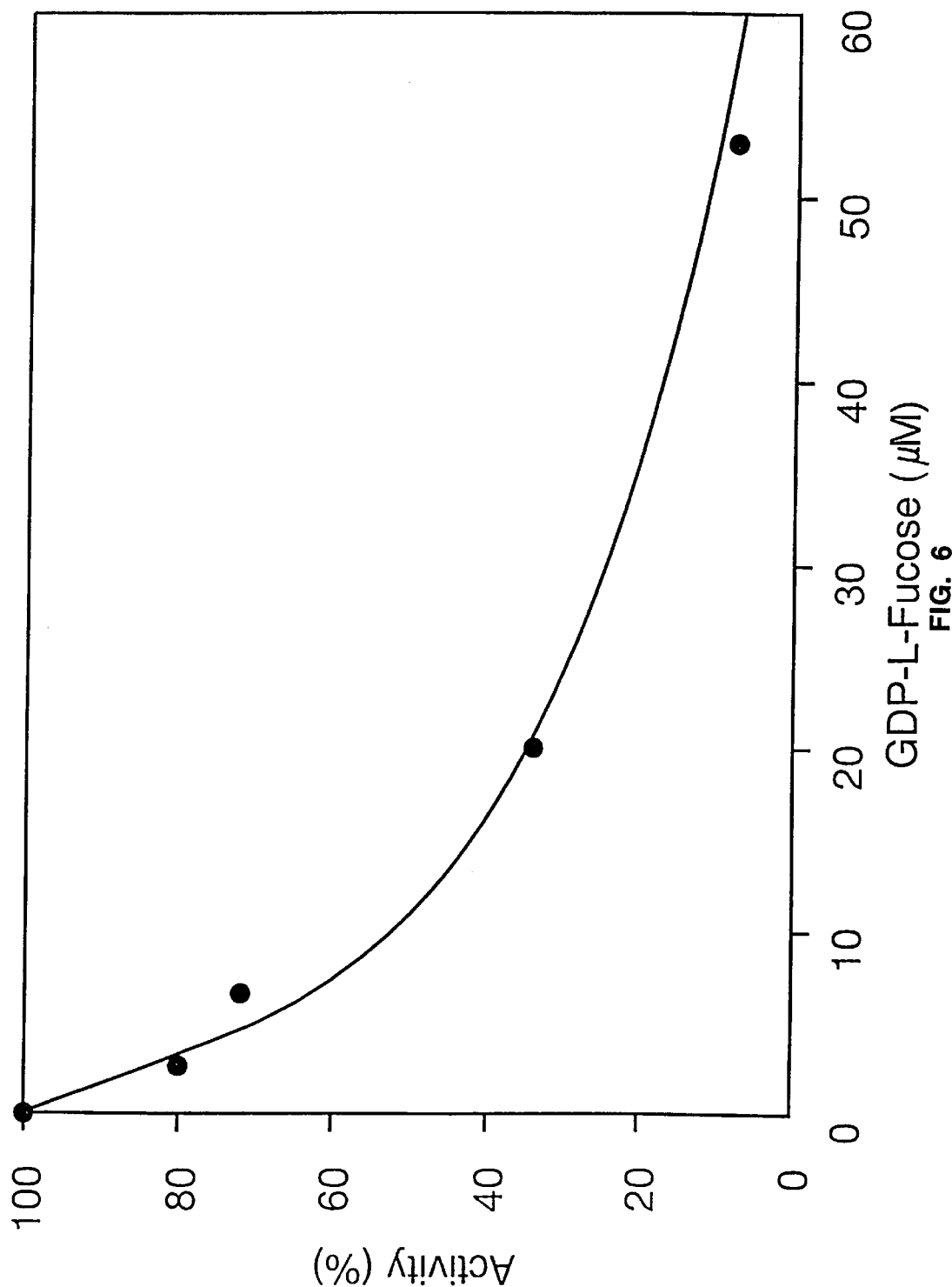
FIG. 6 shows the effect of addition of GDP-L-fucose on the formation of fucose-1-P. Increasing amounts of GDP-L-fucose were added to incubations containing 100 μM [$^3$H] fucose, 5 mM ATP, 5 mM $Mg^{++}$, 65 mM Tris buffer, pH 8.0, and purified enzyme, and the formation of radioactive fucose-1-P was determined by the binding of radioactivity to columns of DE-52.

The kinase was found to be inhibited by the final product of this alternate pathway, GDP-L-fucose. The data in FIG. 6 shows the effect of adding increasing amounts of GDP-L-fucose to reaction mixtures containing L-fucokinase, L-fucose and ATP. It can be seen that the amount of inhibition of fucokinase increased with increasing amounts of GDP-L-fucose, and the $K_i$ for GDP-L-fucose was estimated to be about 10 μM. Other GDP-linked sugars, such as GDP-D-mannose and GDP-D-glucose, did not inhibit the fucokinase, nor did L-fucose-1-P. However, when increasing amounts of GDP-D-mannose were added to incubation mixtures of fucokinase with L-fucose, ATP, $Mg^{++}$ and 20 μM GDP-L-fucose, the presence of GDP-D-mannose effectively blocked the inhibition by GDP-L-fucose, with complete reactivation occurring at about 1 to 1.5 mM GDP-D-mannose (data not shown).

EXAMPLE 19
Tissue Distribution

In order to determine whether the fucokinase was present in other tissues besides kidney, crude cytosolic extracts were prepared from various porcine tissues, and each of these extracts was incubated with [$^3$H]fucose, $Mg^{++}$ and ATP for various times. The amount of label that bound to DE-52 and the specific activity of each extract are presented in TABLE V. It can be seen that L-fucokinase activity was present in many different tissues and in fact, lung and kidney were the tissues with the highest specific activity for this enzyme. Aorta and brain also had reasonably high activity, whereas pancreas, heart and spleen were the lowest. Crude extracts prepared from cultured MDCK cells and HT-29 cells were also assayed but no detectable fucokinase activity was found in those extracts.

TABLE V

Tissue Distribution of Fucokinase

| Tissue | CPM mg/protein | Specific Activity (nmole/mg protein) |
| --- | --- | --- |
| Aorta | 1391 | 0.97 |
| Pancreas | 653 | 0.45 |
| Kidney | 1922 | 1.34 |
| Heart | 485 | 0.33 |
| Lung | 1596 | 1.10 |
| Spleen | 583 | 0.40 |
| Brain | 1261 | 0.87 |
| Liver | 979 | 0.68 |

Reactions contained 100 μM fucose (21,500 cpm), 5 mM ATP with an incubation 15 minutes at 37° C.

EXAMPLE 19
Identification of the Product

The product of the reaction was isolated from large scale incubations of L-fucose with ATP and active enzyme, and was purified by ion-exchange chromatography and by paper chromatography. The radioactive fucose product eluted from the DE-52 column in the same position as authentic sugar-1-P's, such as glucose-1-P or GlcNAc-1-P. The product was subjected to mild acid hydrolysis in 0.05 N HCl at 100° C. Aliquots of the hydrolysis mixture were withdrawn at various times after the initiation of heating, and each aliquot was passed through a column of DE-52. The wash and salt elution of the column were subjected to scintillation counting to determine the rate of hydrolysis. The phosphorylated sugar completely lost its charge (and no longer bound to DE-52), within the first 3 minutes of hydrolysis (data not shown). These data provide convincing evidence that the phosphate group is attached to the anomeric carbon of the sugar.

Figure 7A:
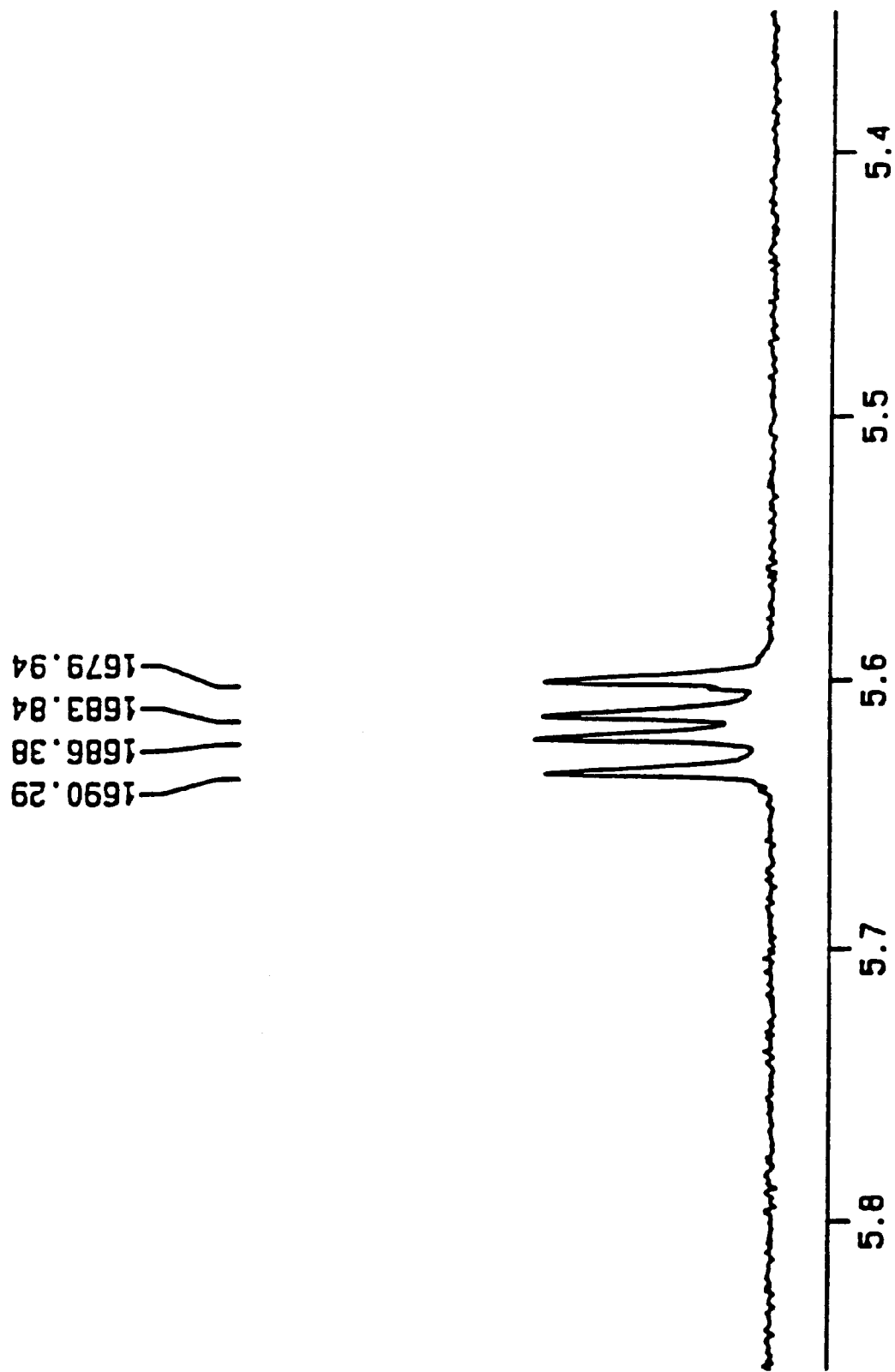
FIG. 7 shows high resolution NMR characterization of the biosynthetic L-fucose-1-P. 300 mHz NMR and $^{31}$P-decoupled (GARP) NMR were performed on a Bruker ARX300 NMR. Data were acquired in $D_2O$ at pH 6.0. The anomeric signal is shown in FIG. 7A, and the GARP-$^{31}$P-decoupling experiment in FIG. 7B.
Figure 7B:
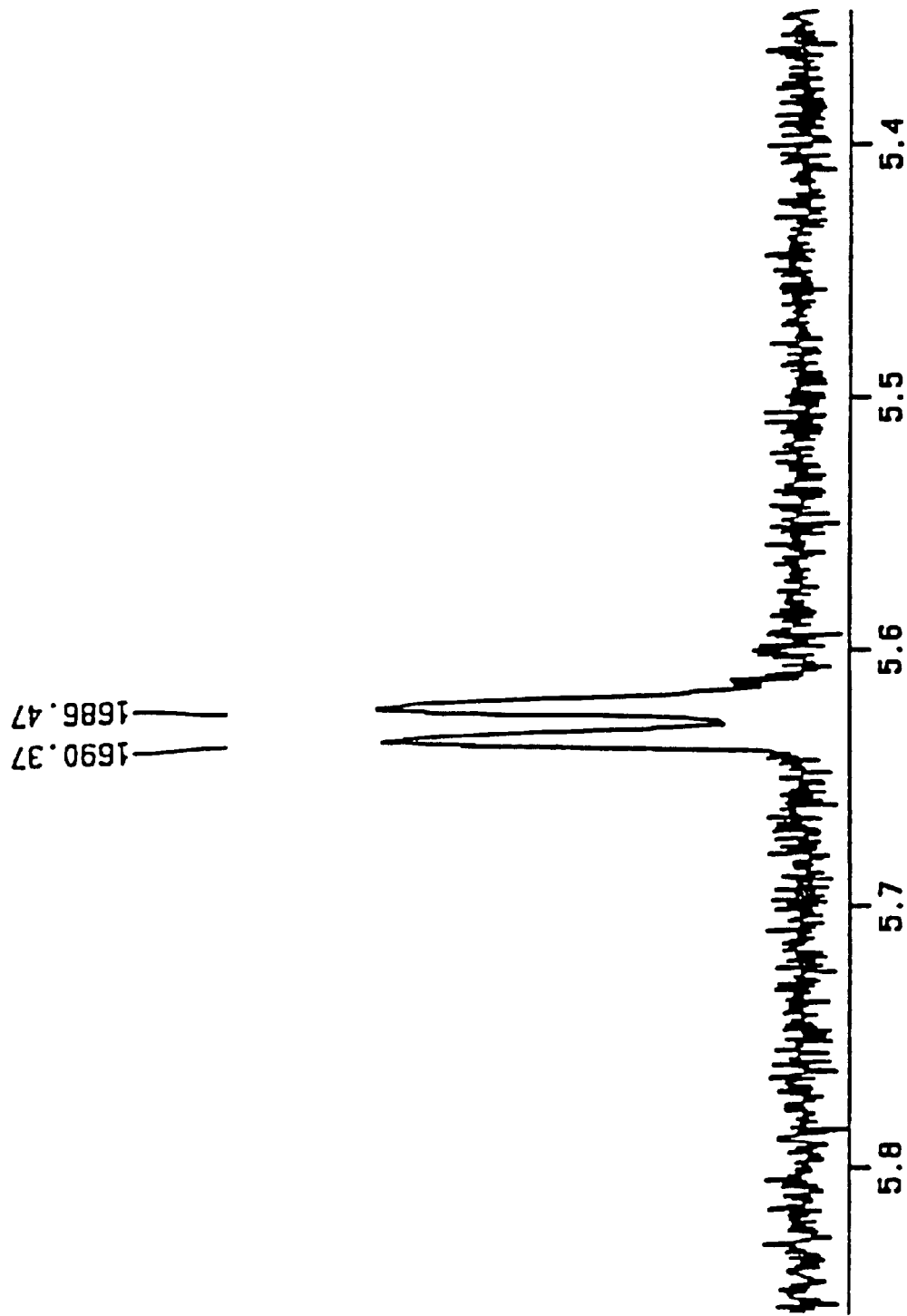

The sugar-1-P produced in the reaction was subjected to 300 mHz NMR as an aide in the structural characterization, as well as to determine the anomeric configuration of the phosphate group. FIG. 7A shows 300 mHz NMR proton detection for the anomeric proton region of L-fucose-1- phosphate, and FIG. 7B shows the $^{31}$P-decoupled spectrum. The $J_{1,2}$ spin-coupling is 4 Hz for the anomeric proton, consistent with a β-L-fucose-1-phosphate configuration.

L-Fucose is an important component of many animal glycolipids and glycoproteins and turnover of these polymers in the lysosomes must lead to the formation of free L-fucose (9). Thus, it is not surprising to find that certain tissues, especially liver and kidney, contain a specific kinase that can phosphorylate L-fucose to form L-fucose-1-phosphate. In fact, early labeling studies in rats indicated that various tissues are capable of utilizing free L-fucose as a precursor of the L-fucose in glycoproteins (9,10), suggesting a pathway to reutilize L-fucose.

The presence of the enzyme L-fucokinase was first demonstrated by Ishihara et al (11) who partially purified this enzyme from pig liver. However, the initial purification of this enzyme was only about 70-fold, and the enzyme preparation still had considerable activity for phosphorylating D-glucose, D-ribose and L-rhamnose. Thus, that enzyme fraction still probably contained hexokinase, ribokinase and other enzymatic activities. Interestingly enough, the kinase was also purified about 3500-fold from pig liver by Yurchenko and Atkinson (18). Their enzyme preparation also phosphorylated D-glucose, D-galactose and D-mannose at about the same rate or better then it phosphorylated L-fucose. These data suggest either that that kinase has a very broad specificity for sugar, or that the preparation was still contaminated with hexokinase and galactokinase. Unfortunately the authors did not examine the nature of the products formed from glucose and mannose to determine whether the phosphate group was in the 1 or 6 position since that would readily have shown whether the reaction was catalyzed by hexokinase. Otherwise it is difficult to envision how a sugar kinase could catalyze a reaction with 4 different sugars, all having a different stereochemistry at carbons 2 through 4.

On the other hand, the L-fucokinase described herein shows very strong specificity for sugars having the L-galactose configuration at carbons 2 through 4. Thus, only L-fucose and D-arabinose were active as phosphate acceptors, although D-arabinose was only about 10% as effective as L-fucose. In addition, the enzyme only utilized ATP as the phosphate donor in contrast to the enzyme reported by Ishihara et al (11) which could also use CTP, UTP and GTP as phosphate donors. The enzyme of the present invention has been purified much more extensively to apparent homogeneity. Amino acid sequencing of the purified enzyme produced the sequences of three peptides. These sequences do not show any more then 40% homology to known sequences by the BLAST search. Thus, this protein is clearly not closely related to other reported kinases.

The following references were cited herein:
1. Fukuda, M., in "*Molecular Glycobiology*", (Fukuda, & Hindsgaul, eds.), pp. 1–52, Oxford University Press, Oxford, U.K. (1994)
2. Watkins, W. M., *Adv. Human Genet.* 10:1–136, (1980).
3. Lowe, J. B., et al, *Cell* 63:475–484, (1990).
4. Lasky, L. A., *Science* 258:964–969, (1992).
5. Ginsburg, V., *J. Biol. Chem.* 235:2196–2205, (1960).
6. Foster, D. W., et al., *Biochem. Biophys.* Acta 54:376–386, (1961).
7. Wilkinson, J. F., *Nature* 180:995–999, (1959).
8. Heath, E. C., et al., *J. Biol. Chem.* 230:511–517, (1958).
9. Coffey, J. W., et al., *J. Biol. Chem.* 239:4011–4019, (1964).
10. Bekesi, J. G., et al., *J. Biol. Chem.* 242:3873–3879, (1967).
11. Ishihara, H., et al., *J. Biol. Chem.* 243:1103–1109, (1968).
12. Ishihara, H., et al., *J. Biol. Chem.* 243:1110–1115, (1968).
13. Cuatrecasas, P., *J. Biol. Chem.* 245:3059–3065, (1970).
14. Yon, R. J., *Biochem.* J. 126:765–767, (1972).
15. Laemmli, U. K., *Nature* 227:680–685, (1970).
16. Haley, B. E., *Meth. Enzymol.* 200:477–487, (1991).
17. Bradford, M. M., *Anal. Biochem.* 22:248–254, (1976).
18. Yurchenco, P. D., et al., *Biochemistry* 14:3107–3114, (1975).

Any patents or publications mentioned in this specification are indicative of the levels of those skilled in the art to which the invention pertains. These patents and publications are herein incorporated by reference to the same extent as if each individual publication was incorporated by reference.

One skilled in the art will readily appreciate that the present invention is well adapted to carry out the objects and obtain the ends and advantages mentioned, as well as those inherent therein. These examples along with the methods, treatments, molecules, and specific compounds described herein are presently representative of preferred embodiments, are exemplary and are not limitations on the scope of the invention. Changes therein and other uses will occur to those skilled in the art which are encompassed within the spirit of the invention as defined by the claims.

What is claimed is:

1. The enzyme L-fucokinase in an isolated and homogeneously purified form, wherein said enzyme in its native state has a molecular weight of 440 kilodaltons based on gel filtration, an optimal pH of about 8.0, and wherein said enzyme has the activity to catalyze the phosphorylation of L-fucose but does not phosphorylate D-glucose, D-galactose and D-mannose.

2. The enzyme of claim 1, wherein said enzyme is isolated and purified to homogeneity from pig kidney.

3. The enzyme of claim 1, wherein the enzymatic activity of said enzyme increases in the presence of a divalent cation, wherein said divalent cation is selected from the group consisting of magnesium and iron.

4. The enzyme of claim 1, wherein said enzyme has a decreased activity in the presence of a divalent cation selected from the group consisting of copper, zinc and mercury compared with its activity when in the presence of magnesium or iron.

5. The enzyme of claim 1, wherein said enzyme requires magnesium for optimal activity.

6. The enzyme of claim 1, wherein said enzyme activity is highest with ATP as a nucleoside phosphate donor and wherein said enzyme activity in the presence of a non-ATP nucleoside triphosphate is about 2% of the activity of the enzyme with ATP.

7. The enzyme of claim 1, wherein said enzyme has a catalytic subunit being a protein with a molecular weight of about 110 kDa.

8. The enzyme of claim 1, wherein said enzyme is specific for sugars having an L-galactose configuration at carbons 2, 3 and 4.

* * * * *